Sept. 5, 1967 M. L. MEILLAND Plant Pat. 2,765
ROSE PLANT
Filed June 24, 1966
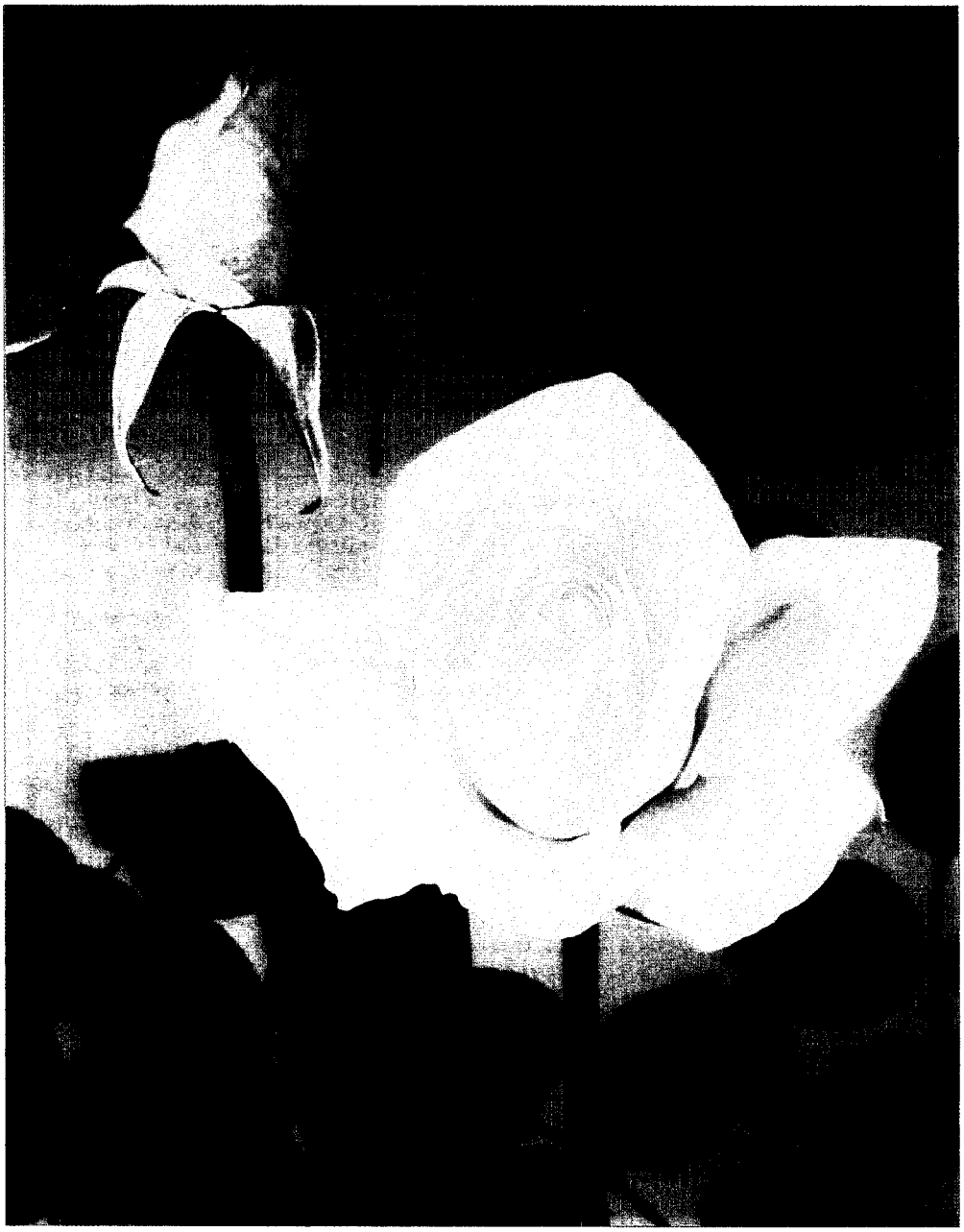
Inventor.
Marie Louise Meilland
By: Robb & Robb
Attorneys.

United States Patent Office

Plant Pat. 2,765
Patented Sept. 5, 1967

2,765
ROSE PLANT

Marie Louise Meilland, Cap d'Antibes, Alpes-Maritimes, France, assignor to The Conard-Pyle Company, West Grove, Pa., a corporation of Pennsylvania

Filed June 24, 1966, Ser. No. 560,395
Claims priority, application France, July 26, 1965, 46,256
1 Claim. (Cl. Plt.—18)

The present invention relates to a new and distinct variety of rose plant of the hybrid tea class, which was discovered by me as a sport of the variety known as "Carina" (U.S. Plant Patent No. 2,378).

At the time of my discovery aforementioned, plants of the variety "Carina" were being grown under my direction and control at Cap d'Antibes, France, and in the course thereof, my attention was attracted to one particular plant which bore flowers of a lighter and more uniform color than those of the parent variety "Carina." Closer observation of this plant showed that it had sported, and I thereupon took steps to preserve the sport, keep it under close observation, and to asexually reproduce the same by budding, as performed at Cap d'Antibes. Continued observations of the sport and the progeny thereof confirmed and definitely established that they were distinguished from the parent variety, as well as from all other rose varieties of which I am aware, as evidenced by the following unique combination of characteristics which are outstanding therein:

(1) A vigorous habit of growth;
(2) Excellent production of flowers when grown under glass for cut flowers;
(3) A large size and attractive shape of the flowers;
(4) A distinctive, attractive, luminous and uniform very light pink general color tonality of the flowers, with equal color intensity both inside and outside thereof; and
(5) Excellent keeping qualities of the flowers as cut flowers.

Asexual reproduction of the new variety by budding, as performed in France, shows that the foregoing characteristics and distinctions some true to form and are established and transmitted through succeeding propagations.

The accompanying drawing shows typical specimens of the vegetative growth and flowers of my new variety in different stages of development and depicted in color as nearly true as it is reasonably possible to make the same in a color illustration of this character.

The following is a detailed description of the new variety, with color terminology in accordance with the Horticultural Colour Chart of the Royal Horticultural Society, except where general color terms of ordinary dictionary significance are obvious:

Type: Hardy; bush; greenhouse; sport; for cut flowers.
Class: Hybrid tea.
Parentage: Sport of "Carina."
Propagation: Holds its distinguishing characteristics through succeeding propagations by budding.

*Flower*

Locality where grown and observed: Cap d'Antibes, France.
Flowers borne: Usually singly to stem; on strong, long stems.
Quantity of bloom: Free, in greenhouse.
Continuity: Continuous.
Fragrance: Slight.
*Nature.*—Tea.
Bud:
*Penducle.*—Long; medium heavy; stiff; almost smooth; with few hairs. Color—Green.

*Before calyx breaks.*—Size—medium large. Form—long; ovoid; with conspicuous neck; with foliaceous appendages on the surface of the bud; with foliaceous parts extending beyond the tip of the bud equal to ¼ or more of its length.
*As calyx breaks.*—Color—Spinel Pink, Plate 0625.
*As first petal opens.*—Size—medium large. Form—ovoid. Color—outside: a little lighter than Tyrian Rose, Plate 24/2.
*Opening.*—Opens up well.
Bloom:
*Size (when fully open).*—Large; from 4¾ to 5½ inches.
*Petalage.*—Double; average of 45 petals.
*Form.*—High-centered at first, but becoming slightly globular; petals being at first tightly rolled outward and retmaining tightly rolled outward at maturity.
Petals:
*Appearance.*—Inside—satiny. Outside—satiny.

This description of a newly opened flower was made from a rose grown in a greenhouse at Cap d'Antibes, France:

*Color.*—Outer petal—outside surface—Neyron Rose, Plate 623/1, suffmore or less with Rose Madder, Plate 23/2 in the veins; inside surface: from Neyron Rose, Plate 623/1 to Neyron Rose, Plate 623/2.
*General color effect.*—Very light pink, with color even and luminous, and of equal intensity both outside and inside.
*Behavior.*—Persist.
*Flower longevity.*—Cut roses grown in greenhouse and kept at living room temperatures—from 5 to 7 days in May.

*Reproductive organs*

Stamens: Many; arranged regularly about pistils; mixed with petaloids.
Filaments: Medium length; most with anthers.
*Color.*—Light pink, becoming white.
Anthers: Small; all open at once.
*Color.*—Reddish-Yellow.
Pollen: Abundant.
Pistils: Many.
Styles: Uneven; medium length; bunched.
Stigma: Color—Yellow.
Ovaries: Protruding from receptacle.
Hips: None observed.
Sepals: Permanent; long; straight.
Seeds: None observed.

*Plant*

Foliage:
*Leaves.*—Compound of 3, 5 and 7 leaflets; normal abundance; moderately large.
*Leaflets.*—Shape—ovoid. Apex—acute. Base—round. Margin—simply serrate. Color—mature: upper surface—from Spinach Green, Plate 0960 to Spinach Green, Plate 0960/1; under surface—a little lighter than Spinach Green, Plate 0960/3.
*Rachis (the supporting stem of the compound leaf).*—Medium heavy. Upper side—grooved. Under side—prickly.
*Stipules.*—Medium long; medium wide; with short points turning out at an angle of 45°.
*Disease resistance.*—Resistant to mildew and blackspot, as determined by comparison with the average rose variety grown under the same cultural conditions at Cap d'Antibes, France.
Growth:
*Habit.*—Bushy; upright; much-branched.

*Growth.*—Vigorous.
*Canes.*—Heavy.
*Main stems.*—Color—Spinach Green, Plate 0960/2.
Prickles—Color—Brown.
*Branches.*—Color—Spinach Green, Plate 0960/2.
*New shoots.*—Color—Lettuce Green, Plate 861.
Prickles—Color: Green.

I claim:

A new and distinct variety of rose plant of the hybrid tea class, substantially as herein shown and described, characterized particularly as to novelty by the unique combination of a vigorous habit of growth, excellent production of flowers when grown under glass for cut flowers, a large size and attractive shape of the flowers, a distinctive, attractive, luminous and uniform very light pink general color tonality of the flowers, with equal color intensity both inside and outside thereof and excellent keeping qualities of the flowers as cut flowers.

No references cited.

ABRAHAM G. STONE, *Primary Examiner.*
ROBERT E. BAGWILL, *Examiner.*